United States Patent [19] [11] Patent Number: 4,885,280
Jarreau et al. [45] Date of Patent: Dec. 5, 1989

[54] NOVEL 14-AMINO STEROIDS

[75] Inventors: Francois-Xavier Jarreau, Versailles; Jean-Jacques Koenig, Vernou la Celle S/Seine, both of France

[73] Assignee: Norwich Eaton Pharmaceuticals, Inc., Norwich, N.Y.

[21] Appl. No.: 252,240

[22] Filed: Sep. 30, 1988

[51] Int. Cl.[4] .......................... C07J 1/00; C07J 41/00; C07J 17/00; A61K 31/58
[52] U.S. Cl. ........................................ 514/26; 536/5; 540/106; 540/118; 514/172
[58] Field of Search .................... 540/106, 118; 536/5; 514/26, 172

[56] References Cited

U.S. PATENT DOCUMENTS 3,449,381  6/1969  Bowers ............................. 540/118
3,634,409  1/1972  Cross ............................... 540/118
4,552,868 11/1985  Jarreau ............................. 514/26

Primary Examiner—Douglas W. Robinson
Assistant Examiner—Joseph A. Lipovsky
Attorney, Agent, or Firm—David L. Suter; Milton B. Graff, IV; Jack D. Schaeffer

[57] ABSTRACT

The invention relates to androstane-17-carboxylic acid esters, represented by general formula (I):

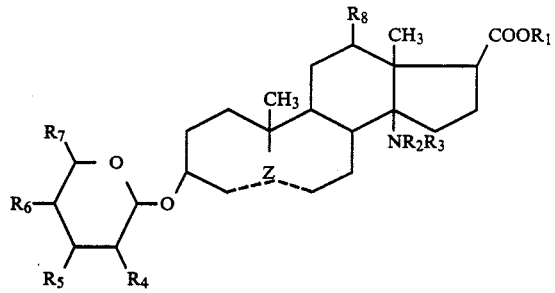

wherein $R_1$ represents a lower alkyl group containing 1 to 4 carbon atoms, a lower alkyl group containing 2 to 4 carbon atoms substituted by an amino group, or an aralkyl group from 6 to 12 carbon atoms, $R_2$ and $R_3$, which may be the same or different, represent a hydrogen atom or a lower alkyl group containing 1 to 4 carbon atoms, $R_4$ represents a hydrogen atom, a hydroxy group or an acetoxy group, $R_5$ represents a hydroxy or acetoxy group, or $R_4$ and $R_5$ represent together a divalent alkylenedioxy group, $R_6$ represents a hydroxy group, a methoxy group, or an acetoxy group, $R_7$ represents a methyl group or a hydroxymethyl group, $R_8$ represents an hydrogen atom or a hydroxy group and $$\overset{|}{Z}$$

represents either a $$-\overset{|}{C}H-$$

group or a $$=\overset{|}{C}-$$

carbon atom having the double linkage in the 4- or 5-position of the steroid nucleus.

Such esters are prepared by coupling reaction of the corresponding 14-azido-derivatives with a sugar, followed by a reduction.

Application in therapy, especially in the treatment of heart failure.

14 Claims, No Drawings

NOVEL 14-AMINO STEROIDS

The present invention relates to new steroid derivatives, and more particularly new androstane 17-carboxylic acid esters substituted at the 3-position by a sugar residue, a process for their preparation, their use in the production of drugs, as well as the drugs containing them.

French patent application No. 2,464,270 describes 14-amino steroid type compounds, and in particular hydroxylated derivatives of 14-amino 21-nor pregnane. In addition, steroid alkaloids of pregnane and androstane substituted at the 14-position by an amino group are well known, for example 14β,20α-pregnanediol is described in A. Astier et al., *Bull. Soc. Chim.*, No. 9–10, pp. 1581–1582 (1976); and other 14β-amino pregnanes and 14β-amino substances are described in A. Astier et al., *Tetrahedron*, Vol. 34, pp. 1481–1486 (1978). However, neither the pharmaceutical properties of these derivatives nor their use in therapy has been described in these documents.

French patent application Nos. 2,531,964 and 2,547,586 describe derivatives of 20-pregnanol, 21-nor 20-pregnanol, 12,20-pregnanediol and 21-nor 12,20-pregnanediol, substituted at the 14-position by an amino group and at the 3-position by a sugar residue. These derivatives possess positive inotropic properties enabling consideration of their use as active ingredients in drugs used in the treatment of congestive heart failure.

East German Pat. No. 138,983 describes cardenolide derivatives, characterized by the presence of a lactone group at the 17-position, and an amino group at the 14-position.

In addition, amino derivatives of steroids which are useful in therapy are known, and for example French patent application Nos. 2,494,697 and 2,494,698 describe 3 (5α)-amino 17α,20-pregnanediol, 3 (5α)-amino 19-nor 20-pregnanol and amino derivatives. These compounds are thought to possess immunotherapeutic properties enabling them to be used as drugs for the treatment of auto-immune disorders resulting from a deficiency in certain lymphocytes.

The work carried out by the applicant has unexpectedly shown that certain androstane 17-carboxylic acid esters, substituted at the 17-position by an alkyl ester group and at the 3-position by a sugar residue, possess much higher and more stable cardiotonic power than known steroid or cardenolide derivatives, while adverse cardiac reactions are diminished.

An object of the present invention therefore is to provide new androstane 17-carboxylic acid esters substituted at the 3-position by a sugar residue, possessing cardiotonic properties.

A further object of the present invention is to provide a process for the preparation of androstane 17-carboxylic acid esters substituted at the 3-position by a sugar residue, from a 14-azido etianic acid ester.

A still further object of the present invention concerns the androstane 17-carboxylic acid esters substituted at the 3-position by a sugar residue as cardiotonic medication for the treatment of congestive heart failure, as well as the pharmaceutical compositions containing as an active ingredient at least one of the new androstane 17-carboxylic acid esters substituted at the 3-position by a sugar residue, as well as the use of these derivatives in the production of drugs that can be used in therapy as cardiotonic agents for the treatment of congestive heart failure.

The new androstane 17-carboxylic acid esters substituted at the 3-position by a sugar residue according to the present invention can be represented by the following general formula (I):

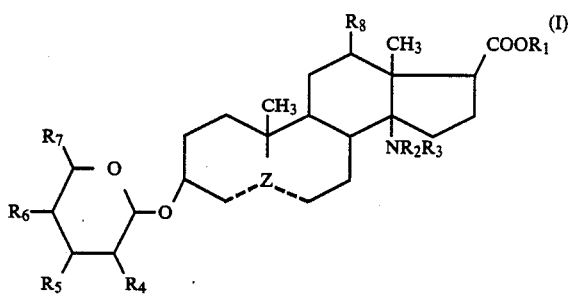

wherein $R_1$ represents a lower alkyl group containing 1 to 4 carbon atoms, a lower alkyl group from 2 to 4 carbon atoms substituted by an amino group, or an aralkyl group from 6 to 12 carbon atoms, $R_2$ and $R_3$, which may be the same or different, represent a hydrogen atom or a lower alkyl group containing 1 to 4 carbon atoms, $R_4$ represents a hydrogen atom, a hydroxy group, or an acetoxy group, $R_5$ represents a hydroxy group or an acetoxy group, or $R_4$ and $R_5$ represent together a divalent alkylenedioxy group, $R_6$ represents a hydroxy, a methoxy group or acetoxy group, $R_7$ represents a methyl group or a hydroxymethyl group, $R_8$ represents a hydrogen atom or a hydroxy group and

represents either a

group, or a

carbon where the double linkage is at the 4- or 5-position of the steroid nucleus.

In general formula (I) above, the steroid nucleus can be saturated as shown in the following formula (Ia), or comprise a 4–5 or 5–6 double linkage, thus forming a 4- or 5-androstene derivative represented by the following formulae (Ib) and (Ic).

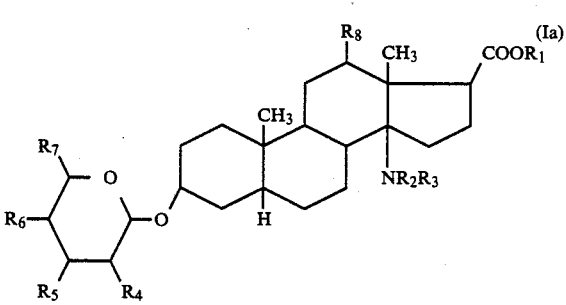

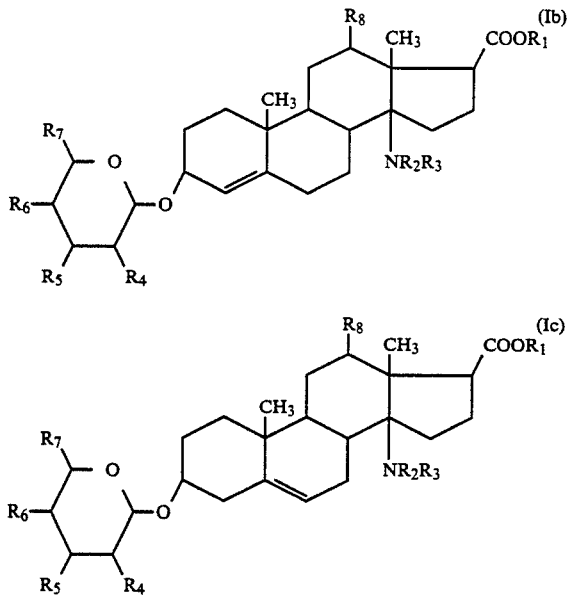

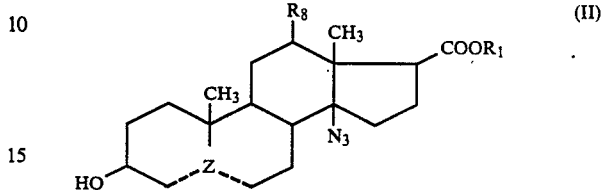

In the following description, the ords "general formula (I)" means the three alternatives (Ia), (Ib) and (Ic), unless otherwise indicated.

In general formula (I) above, the lower alkyl group represented by $R_1$ can be a methyl, ethyl, isopropyl, butyl, etc, and preferably a methyl or ethyl group. The above alkyl group can be substituted by an amino group, thus forming for example a 2-aminoethyl or 3-aminopropyl group, or 3-di-(or mono-)methylaminopropyl group. When $R_1$ represents an aralkyl group, such group can be for example a phenyl group, a benzyl group, a tolyl group, or a phenethyl group. $R_2$ and $R_3$, which may be the same or different, preferably represent a hydrogen atom or a methyl group. When $R_4$ and $R_5$ combine to form a divalent alkylenedioxy group, this group can comprise a linear or branched alkylene moiety containing 1 to 4 carbon atoms, and for example form a methylenedioxy group, an ethylenedioxy group or an isopropylidenedioxy group, $R_8$ preferably represents a hydrogen atom or a hydroxy group.

The new androstane 17-carboxylic acid esters according to the present invention contain several asymmetrical carbon atoms in their molecule and thereby can exist in several stereoisomer forms. The invention of course concerns the new derivatives represented by the above general formula (I) in the form of separate isomers or a combination of one or several isomers.

In particular, the amino group at the 14-position, the ester group at the 17-position and the sugar residue at the 3-position, can have the α or β configuration, but they preferably have the β configuration. In fact, the pharmacological activity of derivatives of general formula (I) has been found to be generally superior when at least one of these three substitutes, and preferably the amino group at the 14-position, have the β configuration, and more particularly when the three substituents have the β configuration.

Among the new androstane 17-carboxylic acid esters represented by general formula (I) above, the invention preferably relates to methyl α-L-rhamnopyranosyloxy-3β amino-14β etianate, methyl α-L-rhamnopyranosyloxy-3β methylamino-14β etianate and methyl α-L-rhamnopyranosyloxy-3β amino-14β etien-4-ate.

As indicated above, the derivatives of general formula (I) according to the present invention can be prepared from a 3-hydroxy-14-azido androstane 17-carboxylic acid ester, represented by the following general formula (II):

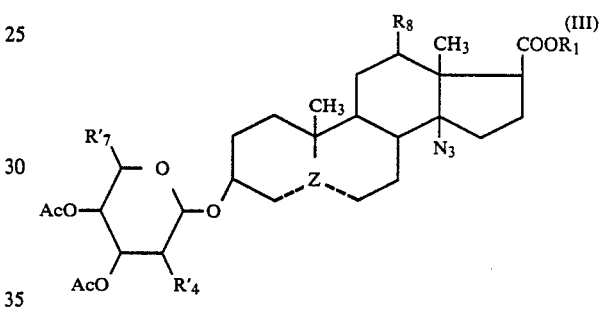

wherein $R_1$ and $R_2$ are as defined in the general formula (I) of claim 1, with an activated sugar residue, thus forming a 3-pyranosyloxy-14-azidoandrostane 17-carboxylic acid ester of the following general formula (III):

wherein $R'_4$ represents a hydrogen atom or an acetoxy group, and $R'_7$ represents a methyl group or a —CH$_2$OAc group, an $R_8$ is as defined in the general formula (I), which is reduced into the derivative of the general formula (I), followed if necessary by an aminomethylation.

The derivatives of the general formula (I) wherein $R_2$ and $R_3$ each represent a hydrogen atom, thus comprising an amino groupe at the 14-position, can be transformed into derivatives comprising a mono- or dialkylamino group by an aminomethylation reaction according to usual techniques.

The 3-hydroxy-14-azido androstane 17-carboxylic acid esters of general formula (II) used as the starting products can easily be obtained from the methyl 3-acetoxy-14-azido-etianate described in French patent application No. 2,464,270, by an ordinary deacetylation reaction, for example by action of an alkaline metal alcoholate such as sodium methanolate, in an appropriate solvent.

The 3-hydroxy-14-azido androstane 17-carboxylic acid ester of general formula (II) comprising a double linkage at the 4–5 or 5–6 -position (Z is =C— or —C=) can be easily prepared from the corresponding ester comprising a saturated steroid nucleus, according to usual techniques for double linkage formation, for example as described by J. Fried and J. A. Edwards *Organic Reaction in Steroid Chemistry*, Van Nostrand Rheinhold Co. (1971) and in the following examples.

The sugar derivative used in the coupling reaction with 3-hydroxy-14-azido androstane 17-carboxylic acid esters is an activated derivative. The activation can, for example be carried out by transforming the sugar into a halogenated or acetylated derivative. The halogenated derivative is preferably a bromide, for example rhamnosyl bromide that is coupled in the presence of mercury cyanide. In the case of activation by acetylation, it is possible to use, for example, tri-O-acetyl-digitoxose that is coupled with methyl 3-hydroxy-14-azido-etianate in the presence of toluene sulfonic acid.

In general, the sugar, activated and protected as above, can be a monosaccharide such as a hexose, a 2-deoxyglucose, a 6-deoxyhexose, a 2,6-dideoxyhexose, etc. More particularly, the monosaccharide can be chosen from among a rhamnose, a glucose, an arabinose, a digitoxose, a fructose, a galactose; for example, a rhamnopyrannose, a hexopyrranose, a 6-deoxy-glucose, a 4,6-dideoxy-glycopyranose, etc, can be used. A rhamnose is preferably used, and more particularly a rhamnopyranose. Of course, it is possible to use different existing anomers, and preferably the $\alpha$-L and $\beta$-forms.

The hydroxyl functions of the sugar are previously protected in the usual manner before carrying out the coupling reaction, for example by acetylation or benzoylation. A technique for the protection of the sugars usable in the present invention is described in E. Fisher et al., *Chem. Ber.* 53, p. 2362 (1920). The activated derivative of the thereby protected sugar can be for example 2,3,4-(tri-O-acetyl)-1-bromorhamnose that is coupled in the presence of mercury cyanide, or tri-O-acetyl-digitoxose in the presence of toluene sulfonic acid. The second case gives rise to a combination of isomer glycosides that can be separated by chromatography after deacetylation. When $R_8$ represents a hydroxyl group, such group is also preferably protected by the same techniques.

The protective groups of the sugar derivatives can then be eliminated by means of the usual techniques, after coupling with the 14-azido etianic acid ester, if so desired. For example, deprotection can be carried out by heating in an alkaline medium.

As indicated above, a reduction is carried out after the coupling reaction with the sugar derivative in order to obtain the derivative of general formula (I). The reduction of methyl 3-pyranosyloxy-14-azido-etianate of general formula (III) is carried out by action of sodium borohydride in the presence of tellure in an alcohol, followed if necessary by deacetylation.

According to an alternative, the reduction of methyl 3-pyranosyloxy-14-azido-etianate of general formula (III) is carried out by hydrogenation reaction in the presence of Raney nickel, preceded if necessary by deacetylation.

The following examples provide a more detailed illustration of the invention without limiting the scope there of.

EXAMPLE 1

Methyl 3$\beta$-($\alpha$-L-rhamnopyranosyloxy)-14$\beta$-amino-etianate

A solution is prepared containing 20 g of methyl 3$\beta$-hydroxy-14$\beta$-azido-etianate and 37.6 g of 2,3,4-(tri-O-acetyl)-1-bromo rhamnose in 1.5 liters of acetonitrile extemporaneously distilled on $P_2O_5$. 26.7 g of mercury cyanide is added. The solution is shaken at room temperature for about one hour.

The reactive medium is then poured into 650 ml of a saturated solution of sodium hydrogenocarbonate. This solution is shaken for 50 min., then 500 ml of toluene is added. The aqueous phase is extracted three times with toluene, washed with water, then with water saturated with sodium chloride.

The toluene phases are collected, dried, concentrated until dry. After recrystallization in methanol, 26.2 g (76% yield) of white crystals of methyl 3$\beta$-(tri-O-acetyl $\alpha$-L-rhamnopyranosyloxy)-14$\beta$-azido-etianate are obtained.

The methyl 3$\beta$-hydroxy-14$\beta$-azido-etianate used as initial product is obtained from a corresponding acetoxylated derivative, by heating in the presence of sodium methanolate, extraction and crystallization in hexane.

In a one liter balloon-flask, a mixture of 8.7 g of sodium borohydride and 12.3 g of ground tellure, in 313 ml of absolute ethanol extemporaneously distilled on magnesium and degasified with nitrogen, is brought to reflux for about 6 hours under argon.

After cooling at room temperature, 25 g of methyl 3$\beta$-(tri-O-acetyl $\alpha$-L-rhamnopyranosyloxy)-14$\beta$-azido-etianate obtained as indicated above, is progressively added, under inert atmosphere, and kept at room temperature while being shaken for about 20 hours.

The reactive mixture is then shaken in air for 30 minutes, filtered on celite, rinsed with absolute ethanol, and concentrated until dry. The white crystals obtained are picked up with 330 ml of ethyl acetate, then an acid-base extraction is carried out (extraction by 5% sulfamic acid, washing with ethyl acetate, alkalinization, shaking for one hour, extraction with methylene chloride, then washing with water).

After separation of the neutral substances (2.9 g), 14.3 g of bases in the form of white crystals are obtained (raw yield: 75%).

The obtained product, purified by chromatography on Merck silica (solvent: $CH_2Cl_2/MeOH/NH_4OH$ 85/15/1.5 Rf=0.32), then recrystallization in ethanol, is methyl 3$\beta$-($\alpha$-L-rhamnopyranosyloxy)-14$\beta$-amino-etianate.

Melting point: 253°/254° C. (solvent EtOH/H$_2$O).

IR spectrum (Nujol): $\nu$=3370, 3320, 1735, 1605 cm$^{-1}$.

NMR spectrum: (CDCl$_3$+CD$_3$OD 3.5/1). $\delta$=0.91 (s, Me-19) 0.93 (s, Me-18) 1.27 (d, Me-6', J$_{5'-6'}$=6 Hz) 3.68 (s, —COOCH$_3$) 4.80 (H-1') ppm.

EXAMPLE 2

Methyl 3$\beta$-($\alpha$-L-rhamnopyranosyloxy)-14$\beta$-methylamino etianate 0.16 g of the derivative obtained as indicated in example 1 is dissolved in 3.5 ml of acetonitrile and 0.03 ml of a 35% aqueous solution of formaldehyde and 22 mg of sodium borocyanohydride are added. The reaction is allowed to develop for 15 minutes.

155 mg of the methylation product is obtained after neutralization with acetic acid and evaporation of the solvent, recovery of the 2N potash and extraction of the base. The product is separated by chromatography on silica.

Chromatography (T.L.C.): Rf=0.3.
Eluent: $CH_2Cl_2/MeOH/NH_4OH$ (80/20/2).
IR spectrum (Nujol): $\nu$=3700–2300 (max. 3360), 1725, 1695 cm$^{-1}$.

EXAMPLE 3

Methyl 3β-(α-L-rhamnopyranosyloxy)-14β-dimethylamino etianate

This derivative is formed simultaneously with the derivative in example 2 above. It is isolated by chromatography on column and crystallization in ethanol.

Chromatography (T.L.C.): Rf=0.4.

Eluent: CH$_2$Cl$_2$/MeOH/NH$_4$OH (85/15/1.5).

IR spectrum (Nujol): $\nu$=3620–2300 (max. 3550, 3380), 2780, 1735, 1705 cm$^{-1}$.

EXAMPLE 4

Ethyl 3β-(α-L-rhamnopyranosyloxy)-14β-amino etianate 0.3 g of the derivative obtained as indicated in example 1 is allowed to react in 3.5 ml of ethanol containing an equivalent amount of extemporaneously prepared sodium ethanolate.

The reaction is allowed to develop for 24 hours. 0.2 g of pure product consisting of methyl 3β-(α-L-rhamnopyranosyloxy)-14β-amino etianate is obtained after extraction and washing according to the technique described in example 1, then trituration in isopropyl ether and crystallization in ethyl ether.

Chromatography (T.L.C.): Rf=0.25.

Eluent: CH$_2$Cl$_2$/MeOH/NH$_4$OH (85/15/1.5).

IR spectrum (Nujol): $\nu$=3250–3600, 1730, 1700, 1660, 1515, 1040 cm$^{-1}$.

EXAMPLE 5

Methyl 3β-(O-methyl-4'α-L-rhamnopyranosyloxy)14β-amino-5β,17α(H) etianate

The procedure is similar to that indicated in example 1 from methyl 3β-hydroxy-14β-azido etianate but the 2,3,4-tri-O-acetyl)-1-bromo-rhamnose is replaced with 2,3-(di-O-acetyl)-4-methoxy-1-bromo-rhamnose in 1.5 liters of distilled acetonitrile.

Methyl 3β-(O-methyl-4'α-L-rhamnopyranosyloxy)-14β-azido-5β,17α(H) etianate is thereby obtained. 70 mg of the product is put in suspension in 1.5 ml of a mixture consisting of 40 mg of tellurium, 28 mg of sodium borocyanohydride and 1.5 ml of absolute ethanol. The reactive mixture is kept at room temperature with constant stirring for about 21 hours under argon atmosphere.

The excess reagent is destroyed by stirring for 15 minutes in open air. The reactive mixture is then filtered on celite by rinsing with a mixture of methylene chloride and ethanol. 57 mg of base (yield: 85%) are obtained after evaporation of the filtrate until dry, extraction by toluene, washing with a 2% aqueous solution of sulfamic acid, alkalinization and extraction with methylene chloride.

Purification is carried out by chromatography on silica gel column under pressure. The CH$_2$Cl$_2$/EtOH/N$_4$OH mixture (89.1/9/0.9) is used as eluant. 47 mg of methyl 3β-(O-14β-amino-5β,17α(H) etianate (yield: 71%) is obtained after crystallization in isopropanol.

Melting point: F=106°–108° C. (isopropanol solvent).

IR spectrum (Nujol): $\nu$=3700–3100 (max. 3360), 1725, 600, 1195, 1170, 1110, 1045 cm$^{-1}$.

NMR spectrum: (CDCl$_3$/CD$_3$OD). δ=0.90 (s, Me 19), 0.94 (s, Me 19) 1.26 (d, J=6, Me 6'), 2.51 (m, H 17), 3.02 (t, J=9.5, H 4'), 3.54 (s, C-OMe), 3.65 (s, COOMe), 3.4 to 4.1 (m, H 2', 3', 5' and H 3), 4.75 (s, H 1') ppm.

EXAMPLE 6

Methyl 3β-desoxy-6'α-L-tallo-hexopyranosyloxy)-14β-amino-5β,17α(H) etianate 1.8 g of methyl 3β-(tri-O-acetyl-α-L-rhamnopyranosyloxy) 14β-azido etianate, obtained as indicated in example 1, are added to 8.4 ml of 1N sodium methylate under nitrogen atmosphere. 2.5 ml of methanol is then added and the solution is allowed to react for about 1 hour at room temperature.

1.4 g of methyl 3β-(α-L-rhamnopyranosyloxy)-14β-azido etianate is obtained after neutralization with icy acetic acid and extraction with methylene chloride. 0.5 g are removed and dissolved in 4 ml of dimethyl formamide and then 5 ml of dimethoxy-2,2 propane and 15 ml of tosylic acid are added. The solution is left to react for 2 hours at room temperature. 0.4 g of methyl 3β-(O-isopropylidene-2',3' α-L-rhamnopyranosyloxy)-14β-azido-5β,17α(H) etianate (raw yield: 96%) are obtained after evaporation of the solvent and extraction with toluene.

The thereby obtained derivative is purified by chromatography on silica column under pressure by eluting with the CH$_2$Cl$_2$/EtOH (98/2) mixture (Rf=0.65).

IR spectrum (Nujol): $\nu$=3650–3250 (max. 3470), 2110, 1740 cm$^{-1}$.

0.1 ml of dry dimethylsulfoxide is added to a solution consisting of 0.1 ml of oxalyl chloride in 2.1 ml of methylene chloride cooled to −60° C. The solution is stirred for 5 minutes at −60° C. and then for 5 minutes at −40° C. 100 mg of methyl 3β-(O-isopropylidene-2',3' α-L-rhamnopyranosyloxy)-14β-azido-5β,17α(H) etianate, obtained as indicated above, dissolved in 0.7 ml of methylene chloride, is added drop by drop.

The mixture is allowed to react under constant stirring for one hour at −40° C. The reaction is then stopped by adding 0.6 ml of N,N-diisopropylethylamine.

The mixture is allowed to return to room temperature. The solvent is evaporated under vacuum in order to obtain the methyl 3β-(deoxy-6' O-isopropylidene-2',3' α-L-lyxohexopyranulos-4'-yloxy)-14β-azido-5β,17α(H) etianate.

6.7 g of sodium borohydride is added to a solution cooled to 0° C. of 100 mg of the derivative obtained as indicated above and 66 mg of CeCl$_3$7H$_2$O in 0.5 ml of methanol. The resulting suspension is kept at room temperature for one hour while stirring. After extraction by methylene chloride and washing with water saturated with sodium chloride, the residue is purified by chromatography on silica column under pressure by eluting with the CH$_2$Cl$_2$/EtOH (98/2) mixture (Rf=0.46).

The methyl 3β-(desoxy-6' O-isopropylidene-2',3' α-L-tallo-hexopyranosyloxy)-14β-azido-5β,17α(H) etianate obtained (70 mg) is hydrolyzed in solution in 1.4 ml of chloroform by 0.16 ml of trifluoroacetic acid in the presence of about 1% water. After extraction by the chloroform, 70 mg of crystallizable dry residue in methanol is obtained, consisting of the methyl 3β-(deoxy-6' α-L-tallo-hexopyranosyloxy)-14β-azido-5β,17α(H) etianate.

The thereby obtained derivative is reduced with a mixture of sodium borohydride (26 mg), ground tellurium (37 mg) and absolute ethanol (2 ml) according to the method described in example 1, by allowing the reaction to continue overnight.

The methyl 3β-(deoxy-6' α-L-tallo hexopyranosyloxy)-14β-amino-5β,17α(H) etianate (isomer of the derivative of example 1) is obtained after filtration, rinsing and extraction as indicated in example 1.

Melting point: F=210° C. (isopropanol solvent).

IR spectrum (Nujol): ν=3600–3050 (3480, 3370, 3100), 1725, 1600 1105, 100, 1050, 1025, 975 cm$^{-1}$.

NMR spectrum: (CDCl$_3$/CD$_3$OD 4/1). δ=0.92 (s, Me-19), 0.94 (s, Me-18) 1.25 (d, J=6, Me 6'), 2.55 (m, H 17), 3.67 (s, OCH$_3$) 4.08 (s, H 1') 7.44 (CHCl$_3$) ppm.

EXAMPLE 7

Methyl 3β-(O-isopropylidene-2',3' α-L-rhamnopyranosyloxy)-14β-amino-5β,17α(H) etianate 150 mg of ground tellurium and 103 mg of sodium borohydride are added to 5.4 ml of absolute ethanol deoxygenized by argon. The solution is heated for 2 hours under ethanol reflux, under argon. 270 mg of methyl 3β-(O-isopropylidene-2',3' α-L-rhamnopyranosyloxy)-14β-azido-5β,17α(H) etianate, obtained as indicated in example 6, in solution in 2 ml of deoxygenized absolute ethanol is added after cooling to room temperature.

The reactive medium is continuously stirred for 24 hours. The reaction is then stopped by exposing to open air for 15 minutes in order to destroy the excess reagent.

The solution is filtered on a celite column and eluted with the CH$_2$Cl$_2$/EtOH (9/1) mixture. The filtrate is then evaporated until dry. The residue is picked up by toluene and the bases are the extracted with a 2% aqueous solution of sulfamic acid. 189 mg of base and 42 mg of a neutral product are obtained after alkalinization with sodium carbonate and extraction with methylene chloride.

By saturating the aqueous phase with sodium chloride, 26 mg of very polar product that is also present in the first basic extract is obtained.

The main basic fraction is purified by chromatography on 5.7 g on silica column under 500 mB of pressure by eluting with the CH$_2$Cl$_2$/EtOH/NH$_4$OH (94.5/5/0.5) mixture.

150 mg of methyl 3β-(O-isopropylidene-2',3' α-L-rhamnopyranosyloxy)-14β-amino-5β,17α(H) etianate (yield: 58%) is thereby obtained in the form of colorless crystals that are soluble in isopropyl ether.

Melting point: F=179° C. (isopropyl ether solvent).

IR spectrum (Nujol): ν=3700–3050 (max. 3350, 3300, 3170), 1735, 1600, 1170, 1075, 1555 cm$^{-1}$.

NMR spectrum: (CDCl$_3$). δ=0.91 (s, Me-19) 0.94 (s, Me-18) 1.25 (d, J=6, Me 6'), 1.36 and 1.51 (2s, CH$_3$—C—CH$_3$) 2.51 (m, H 17), 3.64 (s, OCH$_3$) 3.2 to B 4.2 (m, H 2', 3', 4',5', H 3) 4.99 (s, H1') ppm.

EXAMPLE 8

Methyl 3β-O-(dideoxy-2',6' α-D-ribohexopyranosyloxy)-14β-amino-5β etianate

A solution of 1.6 g of methyl 3β-hydroxy-14β-azido etianate and 2.3 g of tri-O-acetyl digitoxose in the presence of 1.9 g of dry p-toluene sulfonic acid and in 24 ml of benzene is kept while stirring for 2 hours at room temperature.

A residue is obtained after adding an aqueous saturated solution of sodium bicarbonate and extraction by benzene. The residue is purified by chromatography on silica column under pressure, by eluting with the AcO-Et/hexane (25/75) mixture. A mixture of acetylated glycosides is obtained that is subject to a desacetylation reaction with 5.3 ml of sodium methylate. The products are then separated by chromatography on column.

The separated α-D-digitoxoside (T.L.C.: eluant CH$_2$Cl$_2$/MeOH 95/5, Rf=0.57) is used as is in the following reduction stage.

The reduction is carried out according to the technique described in example 1, with the mixture of sodium borohydride, ground tellurium and ethanol.

The methyl 3β-O-(dideoxy-2',6' α-D-ribo-hexopyranosyloxy)-14β-amino-5β-etianate crystals are obtained after extraction as indicated in example 1 and chromatography on silica column, under pressure, by eluting with the CHCl$_3$/EtOH/NH$_4$OH (94.5/5/0.5) mixture and crystallization in the ethyl acetate-isopropyl ether mixture.

Melting point: F=178°–182° C. (ethyl acetate-isopropyl ether solvent).

IR spectrum (Nujol): ν=3250, 3470, 1730 cm$^{-1}$.

NMR spectrum: (CDCl$_3$/CD$_3$OD 4/1). δ=0.94 (s, Me-18 and Me-19) 1.31 (d, J=6, Me 6) 2.52 (m, H-17), 3.11 (dd, J$_{3'4'}$=3, J$_{4'5'}$=10, H4') 3.66 (s, OCH$_3$), 3.95 (H-3, H-3') 4.95 (s, H 1') 7.37 (CHCl$_3$) ppm.

EXAMPLE 9

Methyl 3β-O-(diesoxy-2',6' β-D-ribohexopyranoxyloxy)-14β-amino-5β-etianate

The procedure is indicated in example 8. The β-D-digitoxoside, an isomer of α-D-digitoxoside in example 8, is separated by chromatography.

The thereby obtained β-D-digitoxoside is reduced according to the technique indicated in example 8 with the mixture of sodium borohydride, ground tellurium and ethanol.

The methyl 3β-O-(dideoxy-2',6' β-D-ribo-hexopyranosyloxy)-14β-amino-5β-etianate is obtained after extraction of the bases as indicated in example 1, chromatography on silica column under pressure, by eluting with the CHCl$_3$/EtOH/NH$_4$OH (92.3/7/0.7) mixture and crystallization in the ethyl acetate-isopropyl ether mixture.

Melting point: F=162°–167° C. (ethyl acetate-isopropyl ether solvent).

IR spectrum (Nujol): ν 3600–3040 (3350), 1725, 1595, 1070 cm$^{-1}$.

NMR spectrum: (CDCl$_3$/CD$_3$OD 4/1). δ=0.95 and 0.96 2 (s, Me-18 and Me-19) 1.27 (d, J=6, Me 6'), 2.54 (m, H-17), 3.21 (dd, J$_{3'4'}$=3, J$_{4'5'}$=10 H-4'), 3.70 (s, OCH$_3$), 4.05 (H-3, H-3'), 4.90 (dd, J$_{1'2'a}$=10, J$_{1'2'e}$=2, H 1') 7.52 (CDCl$_3$) ppm.

EXAMPLE 10

Methyl O-3β-(dideoxy-2',6'β-D-arabino-hyxopyranosyloxy)-14β-amino-5β,17α(H)-etianate Tri-O-acetyl digitoxoside is coupled with methyl 3β-hydroxy-14β-azido-etianate as indicated in the technique described in example 8. The solution is then saponified by sodium methylate and put through chromatography on silica column under pressure in accordance with the usual technique.

Methyl O-3β-(dideoxy-2',6' β-D-arabino-hexopyranosyloxy)-14β-azido-5β,17α(H) etianate is obtained after extraction and chromatography on silica column under pressure, by eluting with the CH$_2$Cl$_2$/EtOH/NH$_4$OH (89/10/1) mixture.

Melting point: F=210° C. (solvent:isopropanol-isopropyl solvent).

IR spectrum (CHCl$_3$ film):=3700–3100 (3360, 3220), 1700, 1625, 1215 cm$^{-1}$.

NMR spectrum: (CDCl$_3$/CD$_3$OH 4/1). δ=0.93 2 (s, Me-19), 1.01 (s, Me-18) 1.29 (d, J=6, Me 6'), 3.72 (s, OCH$_3$), 4.03 (H-3) 4.56 (dd, J=9, H-1') 7.35 (CHCl$_3$) ppm.

EXAMPLE 11

Methyl O-3β-(dideoxy-2',6'α-D-arabino-hexopyranosyloxy)-14β-amino-5β,17α(H)-etianate The method followed is indicated in example 10. However, the intermediate used is methyl O-3β-(dideoxy-2',6'β-D-arabino-hexopyranosyloxy)14β-azido-5β,17α(H)-etianate, a β-D isomer of the α-D glycoside of example 10, isolated by chromatography from the same reactive mixture.

Reduction in the same conditions indicated in example 10, after chromatography on silica column under pressure, by eluting with the CH$_2$Cl$_2$/EtOH/NH$_4$OH (89/10/1) mixture and crystallization in the CH$_2$Cl$_2$/EtOh mixture produces crystals of methyl O-3β-(dideoxy-2',6'α-D-arabino-hexpy-ranosyloxy)-14β-amino-5β,17(H) etianate.

Melting point: F=270° C. (solvent: methylene chloride-isopropanol).

IR spectrum (Nujol): ν=3500–3150 (3350, 3270), 1730, 1605 cm$^{-1}$.

EXAMPLE 12

Methyl 3β-(α-L-rhamnopyranosyloxy)-14β-amino-4-etianate 5 g of methyl 3β-hydroxy-14β-azido-etianate is treated with 5 ml of Jones reagent in 100 ml of acetone. The reagent is added drop by drop to the solution cooled on an ice-bath. The oxidation reaction is allowed to develop for 20 minutes. 5 g of ketone is obtained after extraction and is crystallized in ethyl acetate (F=189°-191° C.).

The ketone obtained as indicated above is bromated by pouring, one drop at a time, 1.5 g of bromide in solution in 36 ml of dimethyl formamide in a solution of 75 ml of dimethyl formamide containing 2.2 g of ketone, in the presence of 0.07 g of TsOH. The solution is allowed to stand for 6 hours at room temperature. The mixture of two isomers is obtained after extraction and is separated by chromatography on silica column (ethyl acetate/hexane 22/78) in order to yield 1.5 g of methyl 3-oxo-4β-bromo-14β-azido-5β-etianate (the more polar fraction) and 0.5 g of methyl 3-oxo-2β-bromo-14β-azido-5β-etianate (the less polar fraction).

0.8 g of methyl 3-oxo-4β-bromo-14β-azido-5β-etianate in 20 ml of dimethyl formamide is allowed to react with 0.7 g of lithium chloride by heating for 2 hours at 110° C. under nitrogen. 0.5 g of methyl 3-oxo-14β-azido-4-etianate is obtained after extraction and chromatography on silica (ethyl acetate/hexane 28/72) (T.L.C.: ethyl acetate/hexane 1/1, Rf=0.3).

The ketone obtained as indicated above is reduced by allowing 0.5 g of CeCl$_3$ and then 50 mg of NaBH$_4$ react with 0.5 g of ketone in 10 ml of methanol. N hydrochloric acid (pH=6) is used to acidify. Ethyl acetate is used to extract in order to obtain 0.5 g of methyl 3β-hydroxy-14β-azido-4-etianate.

Thin layer chromatography: CH$_2$Cl$_2$/MeOH 97/3, Rf=0.35.

Ir spectrum (Nujol): ν=3300–3600 (3220, 3320,) 2100, 1715, 1665, 1285, 1205, 1180 cm$^{-1}$.

The thereby obtained methyl 3β-hydroxy-14β-azido-4-etianate, analogous to the starting product in example 1 comprising a double bond in the 4-position, is treated as indicated in example 1 with 2,3,4-(tri-O-acetyl)-1-bromo-rhamnose and mercury cyanide in order to form the methyl 3β-(tri-O-acetyl α-L-rhamnopyranosyloxy)-14β-azido-4-etianate.

The methyl 3β-(tri-O-acetyl α-L-rhamnopyranosyloxy)-14β-azido-etianate is desacetlyated by the action of sodium methanolate in methanol at room temperature and then neutralized by dilute hydrochloric acid and extracted by CH$_2$Cl$_2$.

The 14-azido derivative described above is reduced to the corresponding 14-amino derivative by the action of sodium borohydride in the presence of ground tellurium, in absolute ethanol, according to the method described in example 1.

Methyl 3β-(α-L-rhamnopyranosyloxy)-14β-amino-etianate is obtained after chromatography on silica (CH$_2$Cl$_2$/MeOH/NH$_4$OH 85/12/06). It crystallizes in absolute ethanol.

Melting point: F=240°-246° C.

NMR spectrum: (CDCl$_3$+CD$_3$O$_4$ 4/1). δ=1.02 (s, Me-18+Me-19), 1.26 (d, J=6, Me-6'), 2.6 (m, H-17) 3.69 (s, MeO), 4.86 (s, H-1'), 5.26 (s, H-4) ppm.

EXAMPLE 13

Methyl 3β-(α-L-rhamnopyranosyloxy)-14β-amino-5α-etianate 37 mg of the ester of example 12 are treated in the presence of 20 mg of PtO$_2$ according to Adams' reaction. The mixture in suspension in 6 ml of ethyl acetate and 0.6 ml of acetic acid is shaken for 48 hours.

28 mg of product is obtained after extraction according to the usual technique, from the basic fraction. The product is purified by crystallization in isopropyl ether, to yield 16 mg of α-rhanmopyranosyloxy)-14β-amino-5α-etianate.

Melting point: F=206° C.

NMR spectrum: (CHCl$_3$/MeOH 4/1). δ=0.80–0.98 (s, Me-18+Me-19), 1.26 (d, J=6, Me-6'), 2.6 (m, H-17), 3.71 (s, OMe), 4.85 (s, H-1') ppm.

The pharmacological and clinical studies carried out on the new 14-amino etianic acid derivatives according to the present invention have shown that they possess interesting properties enabling their application as active ingredients in drugs used in human and veterinary therapy.

The derivatives according to the invention in particular have a major inotropic effect that is much greater than that of digoxin, a well-known reference drug used in the treatment of congestive heart failure. In addition, their activity is more stable and their cardiac toxicity is lower.

The inotropic activity, demonstrating the cardiotonic power, was verified on the stimulated left auricle in the Guinea-pig, by measuring the force of contraction, according to the technique described in J. Ghysel-Burton et al., Brit. J. Pharmacol., 66, 2, pp. 175–184 (1979).

By way of example, the derivative of example 1 according to the present invention develops a very hight positive maximum inotropic effect (130% at a concentration of $10^{-5}$M), while the inotropic effect of digoxin, in the same conditions, is much lower (70% at a concentration of $10^{-6}$M). In addition, the positive inotropic effect of the derivative complying with the invention is stable for about 60 minutes, whereas digoxin rapidly induces a negative inotropism. This phenomenon indicates lower cell toxicity for the derivative of the invention when compared with digoxin. Similarly, the well-known contacturant effect of digitalis glycosides, and particularly digoxin (refer to *Handbook of Cardiac Glycosides*, Ed. K. Greef), is much lower in the case of derivatives of the invention.

The positive inotropic effect of the derivatives complying with the present invention described in examples 1 to 11 above is indicated in the following table. The inotropic effect is given as a percentage of the increase in the force of contraction of the stimulated left auricle in the Guinea-pig, at a concentration of $5.10^{-6}$M.

| Example | 1 | 2 | 3 | 4 | 5 | 6 | 7 | 8 | 9 | 10 | 11 | 12 | 13 |
|---|---|---|---|---|---|---|---|---|---|---|---|---|---|
| Inotropic effect | 97 | 36 | 17 | 27 | 29 | 34 | 37 | 11 | 35 | 29 | 16 | 95 | 41 |

The positive inotropic effect in the dog anaesthetized with sodium pentobarbital (in vivo tests) is confirmed by the measurement of the hemodynamics parameters, according to the method described in R. E. Patterson et al., *Cardiology*, 57, pp. 277–294 (1972). The product in example 1, after intravenous perfusion of 3 to $4.10^{-9}$ moles per kg.min. for 20 minutes is found to be about 20 to 40%. If the perfusion is continued for several hours at the rate of $2.2.10^{-9}$ moles per kg.min., the cardiotonic activity develops and is maintained at about 60–70%. In the case of digoxin, for a similar inotropic effect, when the perfusion is maintained, heart rhythm troubles appear as of hour 1, then death as of hour 3.

Comparative tests were carried out on 10 dogs for the following therapeutic indexes: A—reversible arrhytmia dose/efficacious dose; B—toxic dose/efficacious dose; C—lethal dose/efficacious dose. The reversible arrhythmia dose is the dose where spontaneously resolving arrhythmia begins; the toxic dose is the dose where the arrhythmia is sustained; the lethal dose is the dose inducing death (no blood pressure and cardiac output); the efficacious dose is the dose where there is a 30% increase in the force of cardiac contraction as compared with the control level.

The results are provided in the following table:

| Substance | Therapeutic Index | | |
|---|---|---|---|
| | A | B | C |
| Digoxin | 1.5 | 2.0 | 3.2 |
| Example 1 | 3.1 | 5.8 | 14.0 |

These results show that the efficacy of the derivatives according to the present invention is superior to that of digoxin and the toxicity is lower.

The androstane 17-carboxylic acid esters according to the present invention can be used as active ingredients in drugs, that can be administered in the usual forms, the active ingredient being diluted in a suitably chosen pharmaceutically acceptable excipient, for example in tablet, capsule or injectable solution form.

The doses administered are comparable to those of the known cardiotonic drugs derived from the cardenolids, and are determined by the physician in the usual manner according to the means of administration and the condition of patient.

What is claimed is:

1. New androstane 17-carboxylic acid esters represented by general formula (I)

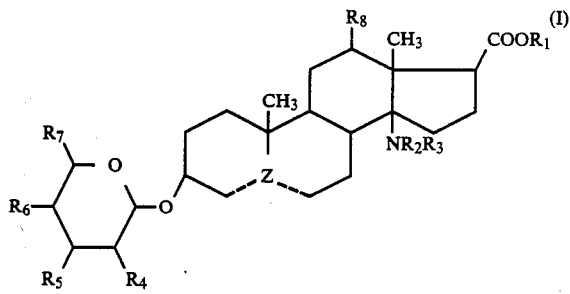

wherein $R_1$ represents a lower alkyl group containing 1 to 4 carbon atoms, a lower alkyl group from 2 to 4 carbon atoms substituted by an amino group, or an aralkyl group from 6 to 12 carbon atoms, $R_2$ and $R_3$, which may be the same or different, represent a hydrogen atom or a lower alkyl group containing 1 to 4 carbon atoms, $R_4$ represents a hydrogen atom, a hydroxy group, or an acetoxy group, $R_5$ represents a hydroxy group or an acetoxy group, or $R_4$ and $R_5$ represent together a divalent alkylenedioxy group, $R_6$ represents a hydroxy a methoxy group or acetoxy group, $R_7$ represents a methyl group or a hydroxy-methyl group, $R_8$ represents a hydrogen atom or a hydroxy group and —Z— represents either a —C— group, or a =C-carbon where the double linkage is at the 4- or 5-position of the steroid nucleus.

2. Androstane 17-carboxylic acid esters according to claim 1, characterized in that $R_1$ is a methyl group or an ethyl group.

3. Androstane 17-carboxylic acid esters according to claim 1, characterized in that $R_5$ and $R_6$ represent a hydroxy group.

4. Androstane 17-carboxylic acid esters according to claim 1, characterized in that $R_4$ and $R_5$ are combined to form an alkylenedioxy group containing 1 to 4 carbon atoms in the alkylene moiety thereof.

5. Androstane 17-carboxylic acid esters according to claim 1, characterized in that $R_4$ represents a hydroxy group.

6. Androstane 17-carboxylic acid esters according to claim 1, characterized in that the amino group at the 14-position, the ester group at the 17-position, and the sugar residue at the 3-position, have the configuration.

7. Androstane 17-carboxylic acid ester according to claim 1, characterized in that they are selected from methyl-L-rhamnopyranosyloxy-3 amino-14 etianate, methyl-L-rhamnopyranosyloxy-3 methylamino-14 etianate and methyl-L-rhamnopyranosyloxy-3 amino-14 etien-4-ate.

8. A pharmaceutical composition, characterized in that it comprises an androstane 17-carboxylic acid ester according to claim 1, as an active ingredient, combined if necessary with one or several pharmaceutical acceptable carriers.

9. A method of treating a human subject having heart failure, by administering an androstane 17-carboxylic acid ester, according to claim 1, to said subject.

10. A process for the preparation of the androstane 17-carboxylic acid esters of claim 1, characterized in that it comprises carrying out a coupling reaction of a 3-hydroxy-14-azido-androstane 17-carboxylic acid ester, represented by the following general formula (II):

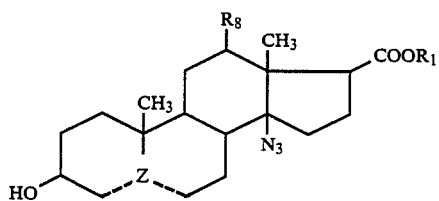

wherein $R_1$ and $R_8$ are as defined in the general formula (I) of claim 1, with an activated sugar residue, thus forming a 3-pyranosyloxy-14-azido-androstane 17-carboxylic acid ester of the following general formula (III):

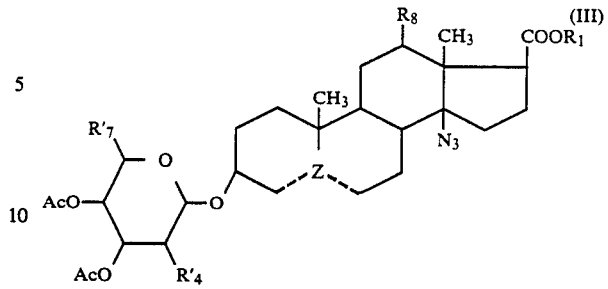

wherein $R'_4$ represents a hydrogen atom or an acetoxy group, and $R'_7$ represents a methyl group or a $-CH_2OAc$ group, an $R_8$ is as defined in the general formula (I), which is reduced into the derivative of general formula (I), followed if necessary by an aminomethylation.

11. The process of claim 10, characterized in that the coupling reaction is carried out between the 3-hydroxy-14-azido-androstane 17-carboxylic acid ester and rhamnosyl bromide in the presence of mercury cyanide.

12. The process of claim 10, characterized in that the coupling reaction is carried out between the 3-hydroxy-14-azido-androstane 17-carboxylic acid ester and tri-O-acetyl-digitoxose in the presence of toluene sulfonic acid.

13. The process of claim 10, characterized in that the reduction of 3-pyranosyloxy-14-azido-androstane 17-carboxylic acid ester of general formula (III) is carried out by action of sodium borohydride in the presence of tellure in an alcohol, followed if necessary by a deacetylation.

14. The process of claim 10, characterized in that the reduction of 3-pyranosyloxy-14-azido-androstane 17-carboxylic acid ester of general formula (III) is carried out by hydrogenation reaction in the presence of Raney nickel, preceded if necessary by a deacetylation.

* * * * *